(12) United States Patent
Park et al.

(10) Patent No.: US 10,066,212 B2
(45) Date of Patent: Sep. 4, 2018

(54) METHOD FOR PREPARING INDUCED PLURIPOTENT STEM CELLS USING SYNTHETIC PEPTIDE

(71) Applicants: Seoul National University R&DB Foundation, Seoul (KR); Nano Intelligent Biomedical Engineering Corporation Co. Ltd., Chungcheongbuk-do (KR)

(72) Inventors: Yoon Jeong Park, Seoul (KR); Chong-Pyoung Chung, Seoul (KR); Jin Sook Suh, Seoul (KR); Jue-Yeon Lee, Gyeonggi-do (KR); Dong Woo Lee, Seoul (KR)

(73) Assignees: Seoul National University R&DB Foundation, Seoul (KR); Nano Intelligent Biomedical Engineering Corporation Co. Ltd., Chungcheongbuk-do (KR)

( * ) Notice: Subject to any disclaimer, the term of this patent is extended or adjusted under 35 U.S.C. 154(b) by 0 days.

(21) Appl. No.: 15/514,337

(22) PCT Filed: Jul. 19, 2016

(86) PCT No.: PCT/KR2016/007857
§ 371 (c)(1),
(2) Date: Mar. 24, 2017

(87) PCT Pub. No.: WO2017/022981
PCT Pub. Date: Feb. 9, 2017

(65) Prior Publication Data
US 2017/0275594 A1  Sep. 28, 2017

(30) Foreign Application Priority Data
Aug. 6, 2015  (KR) ........................ 10-2015-0111223

(51) Int. Cl.
| | |
|---|---|
| *C12N 15/00* | (2006.01) |
| *C12N 5/074* | (2010.01) |
| *C07K 14/00* | (2006.01) |
| *C07K 14/47* | (2006.01) |
| *C12N 5/0775* | (2010.01) |
| *C07K 14/485* | (2006.01) |
| *C07K 14/50* | (2006.01) |
| *C12N 5/00* | (2006.01) |

(52) U.S. Cl.
CPC ............ *C12N 5/0696* (2013.01); *C07K 14/00* (2013.01); *C07K 14/001* (2013.01); *C07K 14/4703* (2013.01); *C07K 14/4723* (2013.01); *C12N 5/0607* (2013.01); *C12N 5/0662* (2013.01); *C07K 14/485* (2013.01); *C07K 14/50* (2013.01); *C12N 5/005* (2013.01); *C12N 5/0037* (2013.01); *C12N 5/0043* (2013.01); *C12N 5/0056* (2013.01); *C12N 2501/998* (2013.01); *C12N 2506/1307* (2013.01); *C12N 2510/00* (2013.01)

(58) Field of Classification Search
CPC ...................................... C12N 5/0696
USPC .................................. 435/325, 455
See application file for complete search history.

(56) References Cited

U.S. PATENT DOCUMENTS
2012/0258539 A1   10/2012  Hu

FOREIGN PATENT DOCUMENTS

| | | | |
|---|---|---|---|
| KR | 10-2015-0025524 A | | 3/2015 |
| WO | 2012144719 A1 | | 10/2012 |
| WO | WO 2011/105869 | * | 10/2012 |
| WO | 2013021212 A2 | | 2/2013 |
| WO | 2014046423 A1 | | 3/2014 |
| WO | WO 2014/046423 | * | 3/2014 |

OTHER PUBLICATIONS

Okita (Nature Methods, 2011, vol. 8, No. 5, p. 409-412).*
Hussein, Current Opinion in Genetics & Development, 2012, vol. 22, p. 435-443.*
Huber, M.A., et al., "NF-B is essential for epithelial mesenchymal transition and metastasis in a model of breast cancer progression", "The Journal of Clinical Investigation", Aug. 2004, pp. 569-581, vol. 114, No. 4.
Li, R., et al., "A Mesenchymal-to-Epithelial Transition Initiates and Is Required for the Nuclear Reprogramming of Mouse Fibroblasts", "Cell Stem Cell", Jul. 2, 2010, pp. 51-63, vol. 7.
Okita, K., et al., "A more efficient method to generate integration-free human iPS cells", "Nature Methods", May 2011, pp. 409-414, vol. 8, No. 5.
Takahashi, K., et al., "Induction of Pluripotent Stem Cells from Mouse Embryonic and Adult Fibroblast Cultures by Defined Factors", "Cell", Aug. 25, 2006, pp. 663-676, vol. 126.
Takahashi, K., et al., "Induction of Pluripotent Stem Cells from Adult Human Fibroblasts by Defined Factors", "Cell", Nov. 30, 2007, pp. 861-872, vol. 131.
Polo, J., et al., "When Fibroblasts Met iPSCs", "Cell Stem Cell", Jul. 2, 2010, pp. 5-6, vol. 7.

* cited by examiner

*Primary Examiner* — Michael C Wilson
(74) *Attorney, Agent, or Firm* — Hultquist, PLLC; Steven J. Hultquist (57) ABSTRACT

Provided is a method of preparing induced pluripotent stem cells using a synthetic peptide, and more particularly, to a method of preparing induced pluripotent stem cells using a peptide capable of inhibiting the activity of NF-κB and promoting mesenchymal-epithelial transition (MET). Since undifferentiated multipotent stem cells may be efficiently prepared under xenopathogen-free or feeder cell-free conditions without requiring co-culture with animal serum or xenogeneic cells, the method for preparing the induced pluripotent stem cells using the synthetic peptide according to the present disclosure is very useful for developing stem cell therapeutic agents that are clinically applicable.

9 Claims, 3 Drawing Sheets
(2 of 3 Drawing Sheet(s) Filed in Color)
Specification includes a Sequence Listing.

REPLACEMENT SHEET

DRAWINGS

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Functional Peptide P1

<400> SEQUENCE: 1

Gly Lys Cys Ser Thr Arg Gly Arg Lys Cys Cys Arg Arg Lys Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Functional Peptide P2

<400> SEQUENCE: 2

Gly Lys Cys Ser Thr Arg Gly Arg Lys Cys Met Arg Arg Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Functional Peptide P3

<400> SEQUENCE: 3

Gly Lys Cys Ser Thr Arg Gly Arg Lys Met Cys Arg Arg Lys Lys
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Control Peptide C1

<400> SEQUENCE: 4

His Arg Arg Cys Asn Lys Asn Asn Lys Lys Arg
1               5                   10

<210> SEQ ID NO 5
<211> LENGTH: 19
<212> TYPE: PRT
<213> ORGANISM: Artificial Sequence
```

```
<220> FEATURE:
<223> OTHER INFORMATION: Control Peptide C1

<400> SEQUENCE: 5

Gly Leu Arg Ser Lys Ser Lys Phe Arg Arg Pro Asp Ile Gln Tyr
1               5                   10                  15

Pro Asp Ala

<210> SEQ ID NO 6
<211> LENGTH: 15
<212> TYPE: PRT
<213> ORGANISM: Artificial Sequence
<220> FEATURE:
<223> OTHER INFORMATION: Formula I
<220> FEATURE:
<221> NAME/KEY: MISC_FEATURE
<222> LOCATION: (10)..(10)
<223> OTHER INFORMATION: Xaa(10) is cysteine (C) or methionine (M)
<220> FEATURE:
<221> NAME/KEY: MISC_FEATURE
<222> LOCATION: (11)..(11)
<223> OTHER INFORMATION: Xaa(11) is cysteine (C) or methionine (M)

<400> SEQUENCE: 6

Gly Lys Cys Ser Thr Arg Gly Arg Lys Xaa Xaa Arg Arg Lys Lys
1               5                   10                  15
```

METHOD FOR PREPARING INDUCED PLURIPOTENT STEM CELLS USING SYNTHETIC PEPTIDE

CROSS-REFERENCE TO RELATED APPLICATIONS

This application is a U.S. national phase under the provisions of 35 U.S.C. § 371 of International Patent Application No. PCT/KR2016/007857 filed Jul. 19, 2016, which in turn claims the priority of Korean Patent Application No. 10-2015-0111223 filed on Aug. 6, 2015. The disclosures of such international patent application and Korean priority patent application are hereby incorporated herein by reference in their respective entireties, for all purposes.

BACKGROUND

Field

The present disclosure relates to a method of preparing induced pluripotent stem cells using a synthetic peptide, and more particularly, to a method of preparing induced pluripotent stem cells using a peptide capable of inhibiting the activity of NF-κB and promoting mesenchymal-epithelial transition (MET).

Description of the Related Art

Stem cells are undifferentiated cells that can be infinitely self-regenerated and differentiated into cells of all tissues in the body, and have received attention as an important target for studying regenerative medicine, the development of cell therapeutic agents such as new drug development, and causes and treatments of human diseases. Embryonic stem cells can be differentiated into various cells and make whole organs, but it is difficult to use them in clinical practice because of the ethical problem that oocytes should be used as cell therapy agents and the immune rejection problem.

In order to solve these problems, a technology for producing induced pluripotent stem cells (iPSC), which are self-regenerative and pluripotent and are characteristics of embryonic stem cells, from differentiated somatic cells by dedifferentiating and reprogramming through an in-vitro culture process was developed for the first time in the world in 2006 by a team led by professor Yamanaka of Kyoto University in Japan (Takahashi, K. et al., Cell 126(4):663-676, 2006; Takahashi, K. et al., Cell 131(5):861-72, 2007). Dedifferentiation means a state in which differentiated cells return to an initial undifferentiated state, and dedifferentiation is performed by "reprogramming" as a series of epigenetic retrogressions. Accordingly, induced pluripotent stem cells (iPSC) mean cells that obtain pluripotency similar to embryonic stem cells which can be differentiated into the cells of all organs configuring the body by externally and artificially stimulating the differentiated somatic cells.

Until now, a method using virus has been the most effective way to introduce a reprogramming gene intracellularly, but the use of a virus to prepare iPSC for treatment has a potential risk, and since the virus enters to the intracellular genome very stably and randomly, various problems such as gene mutation are always inherent. Furthermore, since xenopathogens such as fetal bovine serum (FBS) and mouse embryonic fibroblasts (MEF), which are animal-derived feeder cells, are required in a dedifferentiation-inducing process, and the ultimate use of iPSC is to generate tissues which may be transplanted into the human body, there is a limit to clinical application due to the above risk. In addition, in order to reprogram the differentiated human somatic cells to induced pluripotent stem cells with pluripotency, the current preparation method in which Oct4, Sox2, c-Myc, and Klf4 gene groups, which are embryonic stem cell-specific transcription factors, are used as reprogramming genes to be overexpressed has a problem in that its efficiency is very low at about 0.1% (Takahashi, K. et al., Cell 131:861-872, 2007). Accordingly, in order to apply the induced pluripotent stem cells (iPSC) as a cell therapeutic agent, the development of various reprogramming genes that can dramatically improve dedifferentiation induction efficiency and the development of subsequent technologies that can actually utilize the reprogramming genes in the dedifferentiation process are urgently required.

It was reported recently that NF-κB promotes epithelial-mesenchymal transition (EMT) (Huber, M. A. et al., J. Clin. Invest. 114(4):569-81, 2004), and that Mesenchymal-Epithelial Transition (MET) is essential to dedifferentiate mouse fibroblasts (Li, R. et al., Cell Stem Cell. 7(1):51-63, 2010).

Therefore, in order to develop safe cell therapeutic agents for clinical applications, the inventors exerted all possible efforts to enhance the dedifferentiation-inducing efficiency of induced pluripotent stem cells (iPSC) and as a result, found a functional peptide that inhibits activity of NF-κB protein in the cells, verified that the peptide induces MET to promote dedifferentiation of iPSC, and then completed the present disclosure.

SUMMARY

An object of the present disclosure is to provide a composition for promoting dedifferentiation of induced pluripotent stem cells from differentiated cells comprising a peptide represented by an amino acid sequence of Formula 1 below as an active ingredient.

[Formula 1] (SEQ ID NO: 6)

GKCSTRGRKX$^1$X$^2$RRKK

Where X$^1$ and X$^2$ are cysteine (C) or methionine (M).

Another object of the present disclosure is to provide a method for preparing induced pluripotent stem cells from differentiated cells, comprising (a) introducing a reprogramming gene into differentiated cells; and (b) treating a peptide represented by an amino acid sequence of Formula 1 below in the cells introduced with the reprogramming gene and culturing the cells.

[Formula 1] (SEQ ID NO: 6)

GKCSTRGRKX$^1$X$^2$RRKK

Where X$^1$ and X$^2$ are cysteine (C) or methionine (M).

An aspect of the present disclosure provides a composition for promoting dedifferentiation of induced pluripotent stem cells from differentiated cells comprising a peptide represented by an amino acid sequence of Formula 1 below as an active ingredient.

[Formula 1] (SEQ ID NO: 6)

GKCSTRGRKX$^1$X$^2$RRKK

Where X$^1$ and X$^2$ are cysteine (C) or methionine (M).

Another aspect of the present disclosure provides a method for preparing induced pluripotent stem cells from differentiated cells, comprising (a) introducing a reprogramming gene into differentiated cells; and (b) treating a peptide represented by an amino acid sequence of Formula 1 below in the cells introduced with the reprogramming gene and culturing the cells.

[Formula 1]
(SEQ ID NO: 6)
GKCSTRGRKX$^1$X$^2$RRKK

Where X$^1$ and X$^2$ are cysteine (C) or methionine (M).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Unless otherwise defined, all technical and scientific terms used in this specification have the same meaning as those commonly understood by those skilled in the art. In general, the nomenclature used in this specification is well-known and commonly used in the art.

In the present disclosure, a functional peptide for inhibiting the activity of NFκB protein is found and it is verified that the peptide inhibits epithelial mesenchymal transition (EMT) and furthermore induces mesenchymal-epithelial transition (MET) to promote dedifferentiation.

Accordingly, the present disclosure relates to a composition for promoting dedifferentiation of induced pluripotent stem cells from differentiated cells comprising a peptide represented by an amino acid sequence of Formula 1 below as an active ingredient.

[Formula 1]
(SEQ ID NO: 6)
GKCSTRGRKX$^1$X$^2$RRKK

Where X$^1$ and X$^2$ are cysteine (C) or methionine (M).

In another aspect, the present disclosure relates to a new use of a peptide represented by an amino acid sequence of Formula 1 below for promoting dedifferentiation of induced pluripotent stem cells from differentiated cells.

[Formula 1]
(SEQ ID NO: 6)
GKCSTRGRKX$^1$X$^2$RRKK

Where X$^1$ and X$^2$ are cysteine (C) or methionine (M).

In another aspect, the present disclosure relates to a method for preparing induced pluripotent stem cells from differentiated cells, comprising (a) introducing a reprogramming gene into differentiated cells; and (b) treating a peptide represented by an amino acid sequence of Formula 1 below in the cells introduced with the reprogramming gene and culturing the cells.

[Formula 1]
(SEQ ID NO: 6)
GKCSTRGRKX$^1$X$^2$RRKK

Where X1 and X2 are cysteine (C) or methionine (M).

In the present disclosure, the peptide may be any one selected from the group consisting of SEQ ID NOs: 1 to 3, but is not limited thereto.

Peptide P1:
(SEQ ID NO: 1)
GKCSTRGRKCCRRKK

Peptide P2:
(SEQ ID NO: 2)
GKCSTRGRKCMRRKK

Peptide P3:
(SEQ ID NO: 3)
GKCSTRGRKMCRRKK

In the present disclosure, the peptide has a concentration of preferably 0.01 to 100 μM and more preferably 10 μM, but is not limited thereto. Furthermore, the peptide is preferably treated for 10 days at 24-hr intervals, but is not limited thereto.

In the present disclosure, the differentiated cells are preferably somatic cells or precursor cells, and are preferably derived from the human, but are not limited thereto.

The "somatic cells" of the present disclosure refers to human dermal fibroblasts having a mesenchymal characteristic.

In the present disclosure, it is preferred to use an Eagle's minimum essential medium (EMEM, ATCC 30-2003) for somatic cell culture and use Essential 8 Medium (Gibco, A15169-01) after peptide treatment, but it is not limited thereto.

In the present disclosure, a reprogramming gene may be any one selected from the group consisting of Oct3/4, Sox2, c-Myc, Klf4 and Lin28, but is not limited thereto. A reprogramming gene of Oct3/4, Sox2, Klf4, c-Myc or Lin28 means a gene capable of reprogramming differentiated cells, and in particular, Oct4, Sox2, Klf4 and c-Myc are called Yamanaka genes.

In the present disclosure, according to a known method, the reprogramming genes are divided into three groups and cloned into three different episomal vectors and expressed together with p53 shRNA (pCXLE-hOCT3/4-shp53, pCXLE-hSK, and pCXLE-hUL) to enhance the establishment efficiency of dedifferentiation of stem cells (Okita, K. et al., Nat Methods. 8(5):409-12, 2011).

In the present disclosure, a method of transferring the reprogramming gene to the differentiated cells may use a method of administering a reprogramming gene to a culture medium of differentiated cells, a method of directly injecting a reprogramming gene, or a method of infecting differentiated cells by viruses obtained from packaging cells transfected with a viral vector inserted with a reprogramming gene, but is not limited thereto. As the method of directly injecting the reprogramming gene into the differentiated cells, microinjection, electroporation, insulator, particle bombardment, and the like may be used, but it is not limited thereto.

In the present disclosure, the reprogramming gene is injected by an electroporation method using a nucleofector (Amaxa, US/Nucleofector, Electroporation Gene Transfer, Lonza) instrument from Lonza, and it is preferred that the somatic cells introduced with the reprogramming gene are stabilized by replacing a medium daily for about 3 to 5 days in a culture dish and then treated with the peptide.

The present disclosure may be used as a cell therapeutic agent by preparing the induced pluripotent stem cells under xenopathogen-free or feeder cell-free conditions. In the present disclosure, the problems of the xenopathogen are solved by coating a vitronectin recombinant human protein (VTN-N) on a surface of the culture dish to exclude the use of the feeder cell as a xenogeneic cell. The somatic cells introduced with the reprogramming gene are cultured in a culture dish coated with a vitronectin protein and treated with the functional peptide to promote the efficiency of dedifferentiation into induced pluripotent stem cells.

In the present disclosure, the peptide may be directly treated in a cell culture medium or treated by mixing with a biomaterial for culture, and the biomaterial means a synthetic polymer or a natural polymer. The synthetic polymer in the present disclosure may preferably be poloxamer, polyethylene glycol or polypropylene glycol, and the natural polymer may be vitronectin, collagen, gelatin, alginic acid, chondroitin sulfate, fibronectin or an extracellular matrix protein, but it is not limited thereto. In the present disclosure, vitronectin is used as the natural polymer, and the biomaterial may be used to be coated on a culture container, but it is not limited thereto.

Furthermore, the present disclosure may exclude a xenopathogen generated by supplying various genes from MEF feeder cells to the induced pluripotent stem cell by using a biomaterial for culture capable of replacing mouse embryonic fibroblasts (MEF), which are animal-derived feeder cells used in a conventional culture of induced pluripotent stem cells (iPSC). Therefore, the preparation of iPSC using the peptides of the present disclosure may improve a dedifferentiation-inducing efficiency problem with the xenopathogen problem to be considered to use undifferentiated multipotent stem cells as a cell therapeutic agent.

In the present disclosure, the functional peptide may be characterized by inhibiting nuclear translocation of NF-κB protein in somatic cells into which a reprogramming gene is introduced and inhibiting the activity of the NF-κB by inhibiting an NF-κB signaling mechanism.

In the present disclosure, it is verified that when the peptide is treated with the somatic cells introduced with the reprogramming gene, the nuclear translocation of the NF-κB protein is inhibited by the peptide to inhibit epithelial mesenchymal transition (EMT) and promote mesenchymal-epithelial transition (MET), and thus the dedifferentiation efficiency of the induced pluripotent stem cells (iPSC) from the human somatic cells is increased.

In the present disclosure, the maintenance of the undifferentiated state of the pluripotent stem cells is verified by increased expression of one or more genes selected from the group consisting of alkaline phosphatase (ALP), OCT4, SOX2, human telomerase reverse transcriptase (hERT) and SSEA-4. That is, the somatic cells introduced with the reprogramming gene are treated with the functional peptide, and then an initial process in which a colony is generated in the dedifferentiation process is observed through alkaline phosphatase staining (AP staining), and furthermore, expression of Oct4 is verified by immunofluorescence (IF) using an Oct4 antibody. Finally, the MET degree in the dedifferentiation process of the somatic cells is verified by flow cytometry (FACS) using antibodies of THY1 as a marker of human dermal fibroblasts and an epithelial cell adhesion molecule (EPCAM) as a marker of the epithelial cell.

The present disclosure may improve dedifferentiation-inducing efficiency and the induced pluripotent stem cells prepared by the method are multipotent stem cells in an undifferentiated state which normally represent characteristics as multipotent stem cells. Therefore, the present disclosure is very useful to efficiently prepare multipotent stem cells which are clinically applicable and develop a mass culture system capable of ensuring multipotent stem cell resources which are clinically applicable.

Hereinafter, the present disclosure will be described in more detail with Examples. These Examples are just to exemplify the present disclosure, and it is apparent to those skilled in the art that it is interpreted that the scope of the present disclosure is not limited to these Examples.

Example 1: Synthesis of Dedifferentiation Induction-Promoting Peptide

A peptide P1 (GKCSTRGRKCCRRKK: SEQ ID NO: 1) was synthesized from a C terminal using a synthesis device by an F-moc solid chemical synthesis method. That is, the peptide was synthesized by using Rink resin (0.075 mmol/g, 100 to 200 meshes, 1% DVB crosslinking) bounded with 9-fluorenylmethoxycarbonyl (Fmoc-) as a blocking group, and 50 mg of Rink Amide MBHA resin was added in a synthesizer, the resin was swollen with DMF, and then a 20% piperidine/DMF solution was used to remove the Fmoc-group. In order of the sequence from the C terminal, 0.5 M amino acid solution (solvent: DMF), 1.0 M DIPEA (solvent: DMF&NMP), 0.5 M HBTU (solvent: DMF) were added by 5, 10 and 15 equivalents, respectively, and reacted for 1 to 2 hrs under a nitrogen stream. Whenever the deprotection and the coupling steps were completed, a washing process was performed twice with DMF and methanol. After the last amino acid was coupled, the Fmoc-group was removed by deprotection.

Verification of the synthesis used a ninhydrin test method, and the tested and synthesized resin was dried and shaken with a reagent K cleavage cocktail at a ratio of 20 ml per 1 g of resin for 3 hrs and then the cocktail in which the resin and the peptide were dissolved was separated by filtering. Cold ether was added to the filtered solution and the peptide was crystallized by a solid phase and centrifuged and separated. In this case, the peptide reagent K cleavage cocktail was washed with ether several times and centrifuged to completely remove reagent K cleavage cocktail. The crude obtained above was dissolved in distilled water and separated and purified by using liquid chromatography and the purified peptide was lyophilized.

```
Peptide P1:
                                        (SEQ ID NO: 1)
GKCSTRGRKCCRRKK
```

Furthermore, a peptide P2 (SEQ ID NO: 2) in which the fifth cysteine of C terminal of the peptide P1 (SEQ ID NO:

1) was substituted with methionine and a peptide P3 (SEQ ID NO: 3) in which the sixth cysteine of the C terminal of the peptide P1 (SEQ ID NO: 1) was substituted with methionine were synthesized by a F-moc solid-phase chemical synthesis method using a synthesizer.

```
Peptide P2:
                                       (SEQ ID NO: 2)
GKCSTRGRKCMRRKK Peptide P3:
                                       (SEQ ID NO: 3)
GKCSTRGRKMCRRKK
```

Comparative Example 1: Control Peptide C1 of Functional Peptides P1, P2, and P3

The peptide C1 was synthesized by a F-moc solid-phase chemical synthesis method using the same synthesizer as in Example 1.

```
Peptide C1:
                                       (SEQ ID NO: 4)
HRRCNKNNKKR
```

Comparative Example 2: Control Peptide C2 of Functional Peptides P1, P2, and P3

The peptide C2 was synthesized by a F-moc solid-phase chemical synthesis method using the same synthesizer as in Example 1.

```
Peptide C2:
                                       (SEQ ID NO: 5)
GLRSKSKKFRRPDIQYPDA
```

Example 2: Verification of Induction Efficiency of Peptides for Dedifferentiation of Human Somatic Cells

2-1: Verification of Colony Number of Induced Pluripotent Stem Cells Using ALP Staining In order to verify the dedifferentiation induction efficiency of each peptide, the DNAs of reprogramming genes Oct3/4, Sox2, c-Myc, Klf4, and Lin28 were introduced to human dermal fibroblasts (hDF) of $1.5 \times 10^5$/well on a 6-well coated with 2 g of vitronectin recombinant human protein (VTN-N) by an electroporation method. According to a known method, the reprogramming genes were divided into three groups and cloned into three different episomal vectors and expressed together with p53 shRNA(pCXLE-hOCT3/4-shp53, pCXLE-hSK, and pCXLE-hUL) to enhance the establishment efficiency of dedifferentiation of stem cells (Okita, K. et al., Nat. Methods. 8(5):409-12, 2011). The cells introduced with the reprogramming genes were cultured in an Eagle's minimal essential medium (EMEM, ATCC) and the medium was replaced at 24-hr intervals until cell confluency became 50%. When the confluency became 50%, 10 μM of a dedifferentiation induction-promoting peptide and a control peptide were treated, respectively, and the medium was replaced with Essential 8 Medium and the peptides were treated at the same time as the medium replacement every 24 hrs. The peptide was treated for 10 days at 24-hr intervals, and in order to verify dedifferentiation efficiency per peptide, alkaline phosphatase (AP), known as a marker of embryonic stem cells, was used. For AP staining, an alkaline phosphatase detection kit(Milipore) was used. The medium was removed, 4% paraformaldehyde was added to the cells and they were immobilized for 2 minutes, a Naphthol/Fast Red Violet staining agent was added in a well and reacted at room temperature in a dark space for 20 minutes or more, and then the staining agent was washed with Dulbecco's phosphate buffered saline (DPBS) and the number of stained colonies was verified with a microscope.

Figure 1:
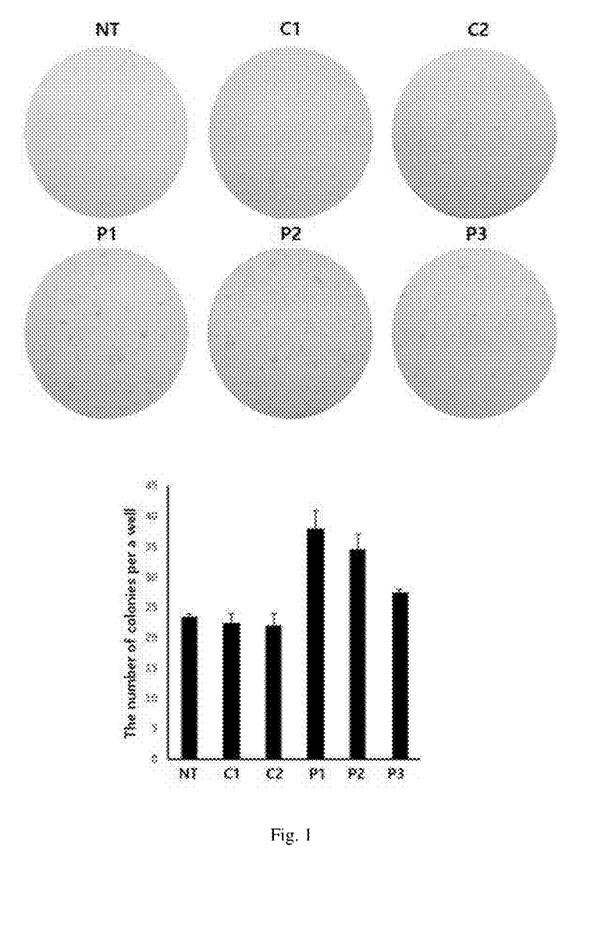
FIG. 1 is a colony staining result verified through alkaline phosphatase staining (AP), after treating functional peptides P1, P2, and P3 and control peptides C1 and C2 for 10 days at 24-hr intervals in human dermal fibroblasts introduced with a reprogramming gene.

As a result, as compared with cells without treating the peptide and control groups treated with peptides C1 or C2, in cells treated with peptides P1, P2, or P3, it was verified that more colonies were stained, as illustrated in FIG. 1. Even in a graph counting and quantifying the number of colonies, similarly, it was verified that the peptides P1, P2, and P3 more efficiently induced dedifferentiation (see FIG. 1).

2-2: Verification of Formation of Induced Pluripotent Stem Cells Using Embryonic Stem Cells Marker Staining Using the same method as in Example 2-1, reprogramming genes were introduced into the cells by an electroporation method in human dermal fibroblasts and divided in a 6-well coated with vitronectin. Thereafter, expression levels of Oct4 as a marker of embryonic stem cells were compared with each other by using an immunofluorescence (IF) method.

The cells treated with 10 μM of each peptide for 10 days were fixed with 4% paraformaldehyde for 10 minutes at room temperature, and then 0.5% Triton-X 100 was added and they were cultured for 15 minutes at room temperature to pass through a cell wall and to penetrate into nuclei in the cells, and blocked with a buffer PBS in which 3% bovine serum albumin (BSA) was dissolved for 30 minutes. An Oct4 primary antibody was diluted with a buffer PBS in which 1% BSA was dissolved at a ratio of 1:100 and reacted for 16 hrs at 4° C. and a secondary antibody bound with fluorescein isothiocyanate (FITC) was diluted at a ratio of 1:200 and reacted for 1 hr at room temperature. Finally, a dye (Hoechst 33342, blue) for staining nuclei was treated for 10 minutes at room temperature and washed with a buffer PBS, and colonies with the clearest fluorescent expression in the well were photographed with a confocal scanning microscope (IX 70, Olympus Co., Tokyo, Japan).

Figure 2:
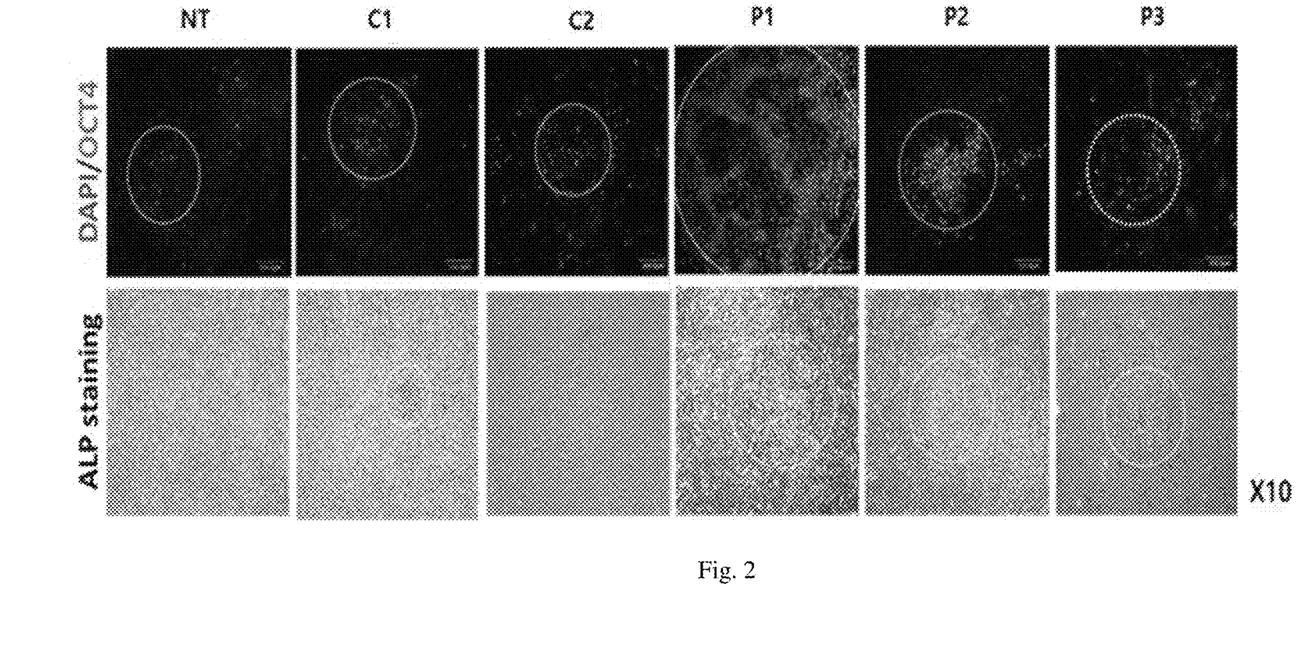
FIG. 2 is a result of verifying the expression of Oct4 as a marker of embryonic stem cells (ES cells) using immunofluorescence (IF) after treating the peptide by the same method as illustrated in FIG. 1.

As a result, as compared with cells without treating the peptide and control groups treated with peptides C1 or C2, in cells treated with peptides P1, P2, or P3, it was verified that more fluorescence was expressed, as illustrated in FIG. 2. It can be seen that an expression amount of the Oct4 as a marker of embryonic stem cells is large and the peptides P1, P2, and P3 promote dedifferentiation. It was verified that the AP staining was clearer in the group treated with the peptides P1, P2, or P3 and the functional peptides P1, P2, and P3 promoted dedifferentiation to colonies as a type of iPSC (see FIG. 2).

2-3: Verification of Difference in Dedifferentiation Induction of Peptides Using Flow Cytometry (FACS)

Using the same method as in Example 2-1, reprogramming genes were introduced into the cells by an electroporation method in human dermal fibroblasts and divided in a 6-well coated with Vitronectin. After 10 days of peptide treatment in which the cells were stabilized, the cells were collected in a 15 ml Falcon tube by using a scrapper and then centrifuged for 3 minutes at 1500 rpm. The cells were washed with a buffer (PBS) and then $1.5 \times 10^5$ cells were transferred to each tube by using cold PBS. THY1 (cat: sc-59398) and EPCAM (cat: ab20160) antibodies at a concentration of 10 μg/ml were diluted with a 3% BSA/PBS solution in the tube and reacted for 30 minutes at 4° C., and then centrifuged three times for 5 minutes at 1500 rpm. After washing with cold PBS, the cells were transferred to a round tube and analyzed by flow cytometry (FACS). Before measuring samples, a control reference value was fixed using THY1 for human dermal fibroblasts and EPCAM for a human mammary epithelial cell (HMEC).

Figure 3:
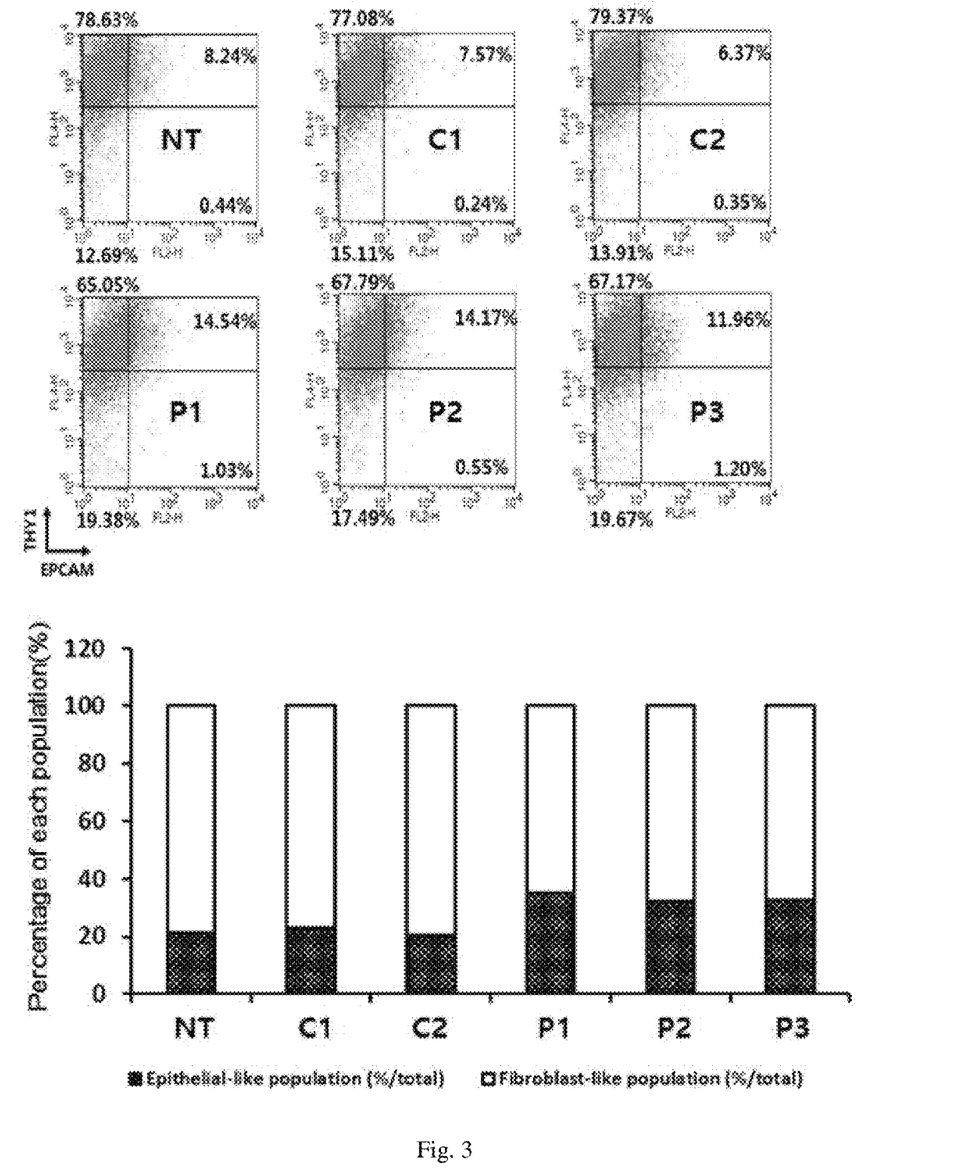
FIG. 3 is a result of verifying the degree of mesenchymal-epithelial transition (MET), which is a dedifferentiation process of differentiated somatic cells, by a marker THY1 of human dermal fibroblasts and an epithelial cell adhesion molecule (EPCAM) as a marker of epithelial cells using flow cytometry (FACS) after treating the peptide by the same method as illustrated in FIG. 1.

As a result, as compared with control groups treated with peptides C1 or C2, in a group treated with peptides P1, P2, or P3, it can be verified that a mesenchymal shape of dermal fibroblasts is significantly changed to an epithelial shape (see FIG. 3).

Although the specific part of the present disclosure has been described in detail, it is obvious to those skilled in the art that such a specific description is just a preferred embodiment and the scope of the present disclosure is not limited. Thus, the substantial scope of the present disclosure will be defined by the appended claims and equivalents thereof.

INDUSTRIAL APPLICABILITY

Since undifferentiated multipotent stem cells may be efficiently prepared under xenopathogen-free or feeder cell-free conditions without requiring co-culture with animal serum or xenogeneic cells, the method for preparing the induced pluripotent stem cells using the synthetic peptide according to the present disclosure is very useful for developing stem cell therapeutic agents that are clinically applicable.

What is claimed is:

1. A method for preparing induced pluripotent stem (iPS) cells, the method comprising:
   (a) introducing one or more nucleic acid sequences encoding reprogramming factors Oct3/4, Sox2 and Klf4 into isolated mammalian somatic cells and then culturing; and
   (b) introducing a peptide having any one of amino acid sequence selected from the group consisting of SEQ ID NOs: 1 to 3 into the isolated mammalian somatic cells to which the reprogramming factor gene has been introduced and then culturing, such that iPS cells are obtained.

2. The method of claim 1, wherein the peptide has a concentration of 0.01 to 100 µM.

3. The method of claim 1, wherein the somatic cells are human somatic cells.

4. The method of claim 1, wherein the iPS cells are prepared under xenopathogen-free or feeder cell-free conditions.

5. The method of claim 1, wherein the reprogramming factor further comprises c-Myc or Lin28.

6. The method of claim 1, wherein step b) comprises introducing the peptide in the presence of a biomaterial.

7. The method of claim 6, wherein the biomaterial is a synthetic polymer or a natural polymer.

8. The method of claim 7, wherein the synthetic polymer is any one selected form the group consisting of poloxamer, polyethylene glycol and polypropylene glycol.

9. The method of claim 7, wherein the natural polymer is any one selected from vitronectin, collagen, gelatin, alginic acid, chondroitin sulfate, fibronectin and an extracellular matrix protein.

* * * * *

UNITED STATES PATENT AND TRADEMARK OFFICE
CERTIFICATE OF CORRECTION

PATENT NO. : 10,066,212 B2
APPLICATION NO. : 15/514337
DATED : September 4, 2018
INVENTOR(S) : Yoon Jeong Park Page 1 of 1

It is certified that error appears in the above-identified patent and that said Letters Patent is hereby corrected as shown below:

On the Title Page

Change 9 Claims to 11 Claims.

In the Claims

Column 11, Line 37, Claim 1:
"any one of" should be -- an --.

Column 12, Line 46, insert the following Claims 10 and 11:
-- 10. The method of claim 1, wherein the peptide inhibits NF- κB activity.
11. The method of claim 1, wherein the peptide promotes mesenchymal-epithelial transition (MET). --.

Signed and Sealed this
Sixteenth Day of April, 2019

Andrei Iancu
*Director of the United States Patent and Trademark Office*